United States Patent [19]

Kisida et al.

[11] Patent Number: 5,356,930
[45] Date of Patent: Oct. 18, 1994

[54] AMIDE DERIVATIVES, THEIR PRODUCTION PROCESSES AND THEIR COMPOSITIONS FOR THE CONTROL OF INSECT PESTS

[75] Inventors: Hiroshi Kisida; Akira Shuto, both of Takarazuka; Noriyasu Sakamoto, Nishinomiya; Noritada Matsuo, Itami; Hiroaki Fujimoto; Kimitoshi Umeda, both of Toyonaka, all of Japan

[73] Assignee: Sumitomo Chemical Company, Limited, Osaka, Japan

[21] Appl. No.: 102,337

[22] Filed: Aug. 5, 1993

Related U.S. Application Data

[63] Continuation of Ser. No. 881,470, May 11, 1992, abandoned.

[30] Foreign Application Priority Data

May 20, 1991 [JP] Japan ................................ 3-145520

[51] Int. Cl.$^5$ ............................................. A01N 37/18
[52] U.S. Cl. ...................................... 514/599; 514/624
[58] Field of Search ............................ 514/599, 624

[56] References Cited

U.S. PATENT DOCUMENTS

| | | | |
|---|---|---|---|
| 4,859,706 | 8/1989 | Buerstinghaus et al. | 514/624 |
| 5,082,852 | 1/1992 | Kardorff et al. | 514/351 |
| 5,132,326 | 7/1992 | Kardorff et al. | 514/599 |
| 5,145,873 | 9/1992 | Kardorff et al. | 514/624 |

FOREIGN PATENT DOCUMENTS

| | | |
|---|---|---|
| 0350688 | 1/1990 | European Pat. Off. |
| 0351617 | 1/1990 | European Pat. Off. |
| 0372330 | 6/1990 | European Pat. Off. |
| 0412391 | 2/1991 | European Pat. Off. |

*Primary Examiner*—Gary E. Hollinden
*Assistant Examiner*—Brian M. Burn
*Attorney, Agent, or Firm*—Birch, Stewart, Kolasch & Birch

[57] ABSTRACT

An amide derivative of the formula:

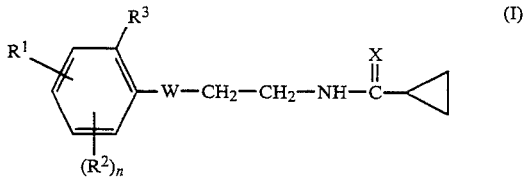

(I)

which is useful for control of insect pests.

3 Claims, No Drawings

AMIDE DERIVATIVES, THEIR PRODUCTION PROCESSES AND THEIR COMPOSITIONS FOR THE CONTROL OF INSECT PESTS

This application is a continuation of application Ser. No. 07/881,470 filed on May 11, 1992, now abandoned.

BACKGROUND OF THE INVENTION

1. Field of the Invention

The present invention relates to amide derivatives, their production processes and their compositions for the control of insect pests.

2. Description of the Prior Art

It is described in U.S. Pat. Nos. 4,859,706 and 4,960,796, European Patents Application Nos. 350,688, 351,617, 372,330 and 412,391 that certain amide compounds are useful as insecticides and acaricides. But, their insecticidal and acaricidal activities are still not satisfactory.

OBJECTS OF THE INVENTION

The main object of the present invention is to provide novel amide compounds having improved insecticidal and acaricidal activities.

This object as well as other objects and advantages of the present invention will become apparent to those skilled in the art from the following description.

SUMMARY OF THE INVENTION

As a result of the extensive study seeking amide derivatives producing a satisfactory controlling effect on insect pests, it has been found that those of the following formula exhibit a remarkable juvenile hormone-like activity and can control significantly the growth of insect pests:

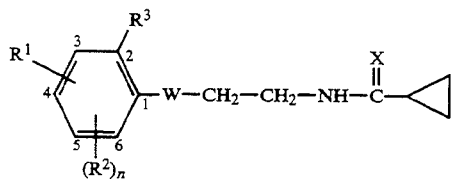

wherein $R^1$ is a group of the formula: $-Y-C_6H_{(5-m)}(R^4)_m$ or a group of the formula: $-Z-R^5$; $R^2$ is, the same or different, a hydrogen atom a halogen atom or a methyl group; $R^3$ is a halogen atom or a $C_1$–$C_3$ alkyl group; $R^4$ is, the same or different, a hydrogen atom, a halogen atom, a $C_1$–$C_3$ alkyl group, a $C_1$–$C_3$ haloalkyl group, a $C_1$–$C_3$alkoxy group, a $C_1$–$C_3$ haloalkoxy group, a cyano group or a nitro group; $R_5$ is a $C_3$–$C_8$ alkyl group, a $C_3$–$C_8$ haloalkyl group, a $C_3$–$C_8$ alkenyl group, a $C_3$–$C_8$ haloalkenyl group, a $C_3$–$C_8$ alkynyl group, a $C_3$–$C_8$ haloalkynyl group, an alkoxyalkyl group having 3 to 8 carbon atoms, a halogenated alkoxyalkyl group having 3 to 8 carbon atoms, a $C_3$–$C_8$ cycloalkyl group, a $C_3$–$C_8$ halocycloalkyl group, a cycloalkylalkyl group having 4 to 9 carbon atoms, a halogenated cycloalkylalkyl having 4 to 9 carbon atoms; W and X are, the same or different, an oxygen atom or a sulfur atom; Y is an oxygen atom, a sulfur atom, a group of the formula: —NH— or a methylene group; Z is an oxygen atom or a single bond; n is an integer of 1 to 3; and m is an integer of 1 to 5.

DETAILED DESCRIPTION OF THE INVENTION

The amide derivatives (I) of the present invention have an excellent juvenile hormone-like activity against insect pests. They exhibit various actions such as metamorphosis inhibition, embryogenesis inhibition and sterilization and are thus efficacious as growth regulators, chemosterilants, ovicides or reproduction inhibitory agents on various insect pests such as agricultural, forestal, hygienic and stored grain insect pests. They are also efficacious against insect pests having an increased resistance to commercial insecticides.

In the formula (I) which represents the amide derivatives of the present invention, examples of the halogen atom represented by $R^2$, $R^3$ and $R^4$ are fluorine chlorine and bromine.

Examples of the $C_1$–$C_3$ alkyl group represented by $R^3$ and $R^4$ are methyl, ethyl, n-propyl and isopropyl.

Examples of the $C_1$–$C_3$ haloalkyl group represented by $R^4$ is trifluoromethyl, difluoromethyl, 2-fluoroethyl, 2,2,2-trifluoroethyl, 2-chloroethyl, 3-fluoropropyl, 2-fluoropropyl, 3-chloropropyl and 3-bromopropyl, etc.

Examples of the $C_1$–$C_3$ alkoxy group represented by $R^4$ is methoxy, ethoxy, n-propoxy and isopropoxy.

Examples of the $C_1$–$C_3$ haloalkoxy group represented by $R^4$ is trifluoromethoxy, difluoromethyl, bromodifluoromethoxy, 2-fluoroethoxy, 2,2,2-trifluoroethoxy, 3-fluoropropoxy, 2-fluoropropoxy, 2-chloroethoxy, 3-chloropropoxy, 3-bromopropoxy and 1,1,2,2-tetrafluoroethoxy, etc.

Examples of the $C_3$–$C_8$ alkyl group represented by $R^5$ is n-propyl, n-butyl, n-pentyl, n-hexyl, n-heptyl, n-octyl, isopropyl, sec-butyl, isobutyl, 2-pentyl, 2-methylbutyl, 3-methylbutyl, 2-ethylpropyl, 3-methyl-2-butyl, neo-pentyl, 2-methyl-2-butyl, 2-hexyl, 2-methylpentyl, 3-methylpentyl, 4-methylpentyl, 2-ethylbutyl, 3-hexyl, 3-methyl-2-pentyl, 4-methyl-2-pentyl, 2,3-dimethylbutyl, 3,3-dimethylbutyl, 2,2-dimethylbutyl, 2-methyl-2-pentyl, 3-methyl-3-pentyl, 2-methyl-3-pentyl and 3,3-dimethyl-2-butyl, etc.

Examples of the $C_3$–$C_8$haloalkyl group represented by $R^5$ is 3-fluoropropyl, 2,2,3,3,3-pentafluoropropyl, 3-chloro-2-butyl, 3-chloropropyl, 2-chloropropyl, 2,3-dichloropropyl, 1,3-dichloro-2-propyl, 3-bromopropyl, 2-bromopropyl, 1-bromo-2-propyl, 2,3-dibromopropyl, 4-fluorobutyl, 4,4,4-trifluorobutyl, 3,3,4,4,4-pentafluoro-2-butyl, 2,2,3,3,4,4,4-heptafluorobutyl, 4-chlorobutyl, 3-chlorobutyl, 2,3,4-trichlorobutyl, 4-bromobutyl, 3-bromobutyl, 5-fluoropentyl, 5-chloropentyl, 5-bromopentyl, 6-fluorohexyl, 6-chlorohexyl, 6-bromohexyl, 7-chloroheptyl and 8-chlorooctyl, etc.

Examples of the $C_3$–$C_8$ alkenyl group represented by $R^5$ is allyl, 2-methylallyl, 1-methyl-2-propenyl, 1,1-dimethyl-2-propenyl, 2-butenyl, 3-butenyl, 2-ethyl-2-butenyl, 2-methyl-2-butenyl, 2-methyl-3-butenyl, 2-pentenyl, 2-hexenyl, 5-hexenyl, 2-ethyl-2-pentenyl, 2-heptenyl and 2-octenyl, etc.

Examples of the $C_3$–$C_8$ haloalkenyl group represented by $R^5$ is 2,3-dichloroallyl, 2,3-dibromoallyl, 2-chloro-2-propenyl, 3-chloro-2-propenyl, 2-bromo-2-propenyl, 2-chloromethyl-2-propenyl, 2-chloro-3-butenyl, 3-chloro-2-butenyl, 4-chloro-2-butenyl, 4-bromo-2-butenyl and 2-chloro-2-octenyl, etc.

Examples of the $C_3$–$C_8$ alkynyl group represented by $R^5$ is 2-propynyl, 1-methyl-2-propynyl, 1-ethyl-2-propynyl, 1-propyl-2-propynyl, 2-butynyl, 1-ethyl-2-butynyl, 1-propyl-2-butynyl, 2-pentynyl, 4-methyl-2-pentynyl, 2-methyl-2-pentynyl, 2-hexynyl, 3-heptynyl, 2-heptynyl and 2-octynyl, etc.

Examples of the $C_3$–$C_8$ haloalkynyl group represented by $R^5$ is 1-chloro-2-propynyl, 1-bromo-2propynyl, 1-chloro-2-butynyl, 1-chloro-2-pentynyl, 1-chloro-2-hexynyl and 1-chloro-2-octyl, etc.

Examples of the alkoxyalkyl group having 3 to 8 carbon atoms represented by $R^5$ is 2-methoxyethyl, 2-ethoxyethyl, ethoxymethyl, isopropoxymethyl, n-propoxymethyl, isobutoxymethyl, 2-isopropoxyethyl, 2-methoxypropyl, 2-methoxybutyl, 2-ethoxypropyl, 2-ethoxybutyl, 2-methoxy-2-methylpropyl, 2-ethoxy-2-methylpropyl, 2-butoxyethyl and 2-hexyloxyethyl, etc.

Examples of the halogenated alkoxyalkyl group having 3 to 8 carbon atoms represented by $R^5$ is 2-(1,1,2,2-tetrafluoroethoxy)ethyl, 2-(2,2,2-trifluoroethoxy)ethyl and 2-difluoromethoxymethyl, etc.

Examples of the $C_3$–$C_8$ cycloalkyl group represented by $R^5$ is cyclopropyl, cyclobutyl, 1-methylcyclopropyl, cyclopentyl, cyclohexyl, 4-methylcyclohexyl, 4-ethylcyclohexyl, 2-methylcyclohexyl and 1-methylcyclohexyl, etc.

Examples of the $C_3$–$C_8$ halocycloalkyl group represented by $R^5$ is 1-chlorocyclopropyl, 2,2-difluorocyclopropyl, 2,2-dichlorocyclopropyl, 3-chlorocyclohexyl, 4-4-chlorocyclohexyl and 1-chlorocyclohexyl, etc.

Examples of the cycloalkylalkyl group having 4 to 9 carbon atoms represented by $R^5$ is cyclopropylmethyl, cyclobutylmethyl, cyclopentylmethyl, cyclohexylmethyl, 2-cyclopropylethyl, 2-cyclohexylethyl, 3-cyclohexylpropyl and 2,2,3,3-tetramethylcyclopropylmethyl, etc.

Examples of the halogenated cycloalkylalkyl group having 4 to 9 carbon atoms represented by $R^5$ is dichlorocyclopropylmethyl and 2,2-dichloro-3,3-dimethylcyclopropylmethyl etc.

Among the amide derivatives (I), preferred are those wherein $R^1$ is a group of the formula: —Y—$C_6H_{(5-m)}$($R^4$)$_m$ or a group of the formula: —Z—$R^5$; $R^2$ is, the same or different, a hydrogen atom, a fluorine atom or a chlorine atom; $R^3$ is a halogen atom; $R^4$ is, the same or different, a hydrogen atom, a halogen atom or a methyl group; $R^5$ is a $C_3$–$C_6$ alkyl group or an alkoxyalkyl group having 3 to 6 carbon atoms; W is an oxygen atom; X is an oxygen atom or a sulfur atom; Y is an oxygen atom or a methylene atom; Z is an oxygen atom or a single bond when $R^5$ is $C_3$–$C_6$ alkyl group, or a single bond when $R^5$ is an alkoxyalkyl having 3 to 6 carbon atoms, n is an integer of 1; m is an integer of 1 or 2.

More preferred are those wherein $R^1$ is a group of the formula: —Y—$C_6H_{(5-m)}$($R^4$)$_m$ or a group of the formula: —Z—$R^5$; $R^2$ is a hydrogen atom; $R^3$ is a chlorine atom; $R^4$ is, the same or different, a hydrogen atom, a fluorine atom, a chlorine atom or a methyl group; is a $R_5$ is a $C_3$–$C_6$ alkyl group or an alkoxyalkyl group having 3 to 6 carbon atoms; W is an oxygen atom; X is an oxygen atom or a sulfur atom; Y is an oxygen atom or a methylene group; Z is an oxygen atom or a single bond when $R^5$ is a $C_3$–$C_6$ alkyl group, or a single bond when $R^5$ is an alkoxyalkyl group having 3 to 6 carbon atoms; n is an integer of 1; m is an integer of 1 or 2.

Most preferred are those wherein $R^1$ is a group of the formula: —Y—$C_6H_{(5-m)}$($R^4$)$_m$ or a group of the formula: —Z—$R^5$; $R^2$ is a hydrogen atom; $R^3$ is a chlorine atom; $R^4$ is, the same or different, a hydrogen atom, a fluorine atom, a chlorine atom or a methyl group; is a $R^5$ is a $C_3$–$C_6$ alkyl group or an alkoxyalkyl group having 3 to 6 carbon atoms; W is an oxygen atom; X is an oxygen atom or a sulfur atom; Y is an oxygen atom or a methylene group; Z is an oxygen or a single bond when $R^5$ is a $C_3$–$C_6$ alkyl group, or single bond when $R^5$ is an alkoxyalkyl group having 3 to 6 carbon atoms; n is an integer of 1; m is an integer of 1 or 2.

The amide derivatives (I) of the present invention can be produced by various processes, among which typical examples are shown below.

Process A The amide derivative (I) is produced by reacting an amine compound of the formula:

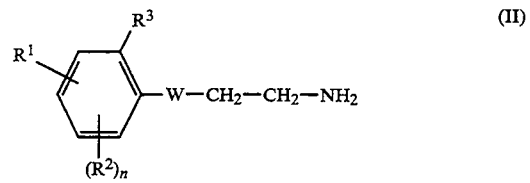

wherein $R^1$, $R^2$, $R^3$, W, X and n are each as defined above with an acid halide of the formula:

wherein L is a halogen atom and X is as defined above.

The reaction may be carried out usually in an inert solvent in the presence of a base at a temperature of from about $-20°$ C. to the boiling point of the solvent, preferably from about $-5°$ C. to the boiling point of the solvent.

The molar proportion of the amine compound (II) and the acid halide (III) to be used for the reaction is not limitative but is preferred to be nearly equal. Examples of the inert solvent are aliphatic hydrocarbons (e.g. hexane, heptane, ligroin, petroleum ether), aromatic hydrocarbons (e.g. benzene, toluene, xylene), halogenated hydrocarbons (e.g. chloroform, carbon tetrachloride, 1,2-dichloroethane, chlorobenzene, 1,2-dichlorobenzene), ethers, (e.g. diethyl ether, diisopropyl ether, dioxane, tetrahydrofuran, ethylene glycol dimethyl ether), ketons (e.g. acetone, methyl ethyl ketone, methyl isobutyl ketone, isophorone, cyclohexanone), esters (e.g. ethyl acetate, butyl acetate), nitro compounds (e.g. nitrobenzene), nitriles (e.g. acetonitrile, isobutylonitrile), tertiary amines (e.g. pyridine, triethylamine, N,N-diethylaniline, tributylamine, N-methylmorpholine), acid amines (e.g. formamide, N,N-dimethylformamide, N,N-dimethylacetoamide), sulfur compounds (e.g. dimethyl sulfoxide, sulfolane), water and mixtures thereof. Examples of the base are organic bases (e.g. pyridine, triethylamine, N,N-diethylaniline), alkali metal hydroxides (e.g. sodium hydroxide, potassium hydroxide), alkali metal carbonates (e.g. sodium carbonate, potassium carbonate, sodium hydrogencarbonate, calcium carbonate), alkali metal hydrides (e.g. sodium hydride), alkali metal alkoxide (e.g. sodium methoxide, sodium ethoxide). When necessary or desired, an ammonium salt such as triethylbenzylammonium chloride and tetrabutylammonium bromide may be added to the reaction system as a catalyst.

After completion of the reaction, post-treatment may follow in a per se conventional manner such as extraction with an organic solvent and concentration. When necessary or desired, the product may further be purified by chromatography, distillation, recrystallization, etc.

Process B

The amide derivative (I) wherein X is a sulfur atom is produced by reacting an amide compound of the for- Among the starting compounds in the above processes, the acid halide (III) is a known compound and available on the commercial market.

The amine compound (II) is obtainable from appropriate commercial products by a conventional procedure as shown below.

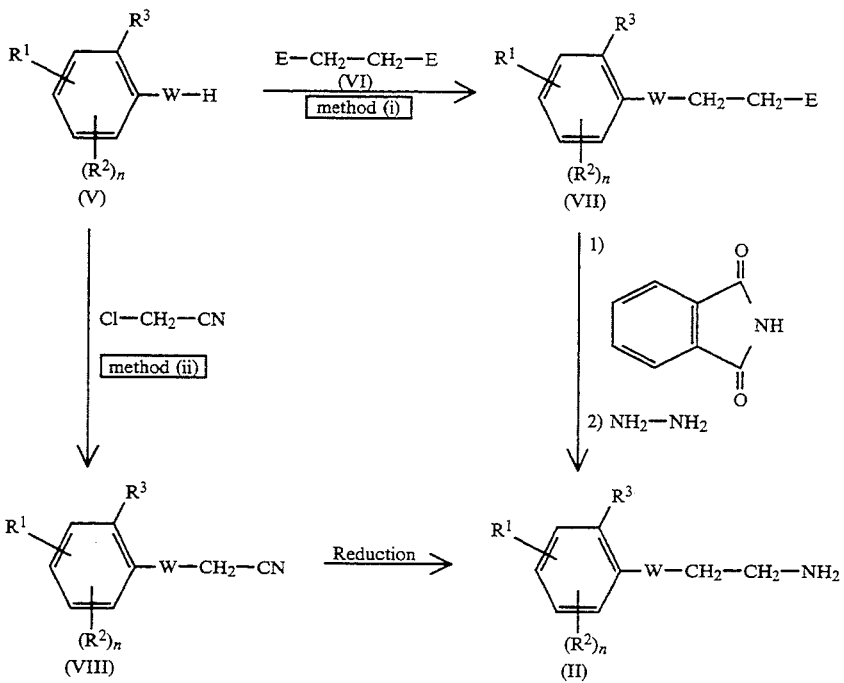

mula:

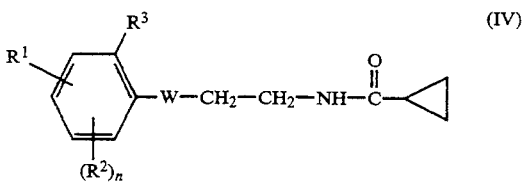

wherein $R^1$, $R^2$, $R^3$, W and n are each as defined above with phosphorus pentoxide or a Lawesson's reagent.

The reaction may be carried out usually in an inert solvent in the presence of a catalyst at a temperature of from about 0° C. to the boiling point of the inert solvent, preferably from about a room temperature to the boiling point of the inert solvent.

The molar proportion of the amide compound (IV) and phosphorus pentoxide or a Lawesson's reagent is not limitative but is preferred to be nearly equal.

The Lawesson's reagent described above means a compound having the formula: $(CH_3OC_6H_4PSS)_2$. Examples of the inert solvent are aromatic hydrocarbons (e.g. benzene, toluene, xylene), aliphatic hydrocarbons (e.g. hexane, heptane), pyridines (e.g. pyridine, picoline) and mixtures thereof.

After completion of the reaction, post-treatment may follow in a per se conventional manner such as extraction with an organic solvent and concentration. When necessary or desired, the product may further be purified by chromatography, distillation, recrystallization, etc.

wherein $R^1$, $R_2$, $R^3$, W and n are each as defined above and E is a halogen atom.

The two kinds of methods (i) and (II) in the above processes can be used properly according to $R^1$ of the (thio)phenol compound (V). Examples of the halogen atom represented by E are, the same or different, chlorine, bromine and iodine.

Method (i):

The amine compound (II) is produced by reducing the ethyl halide compound of the formula:

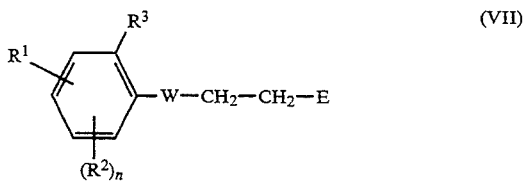

wherein $R^1$, $R^2$, $R^3$, W, n and E are each defined above. Furthermore, the ethyl halide compound (VII) is produced by reacting the (thio)phenol compound of the formula:

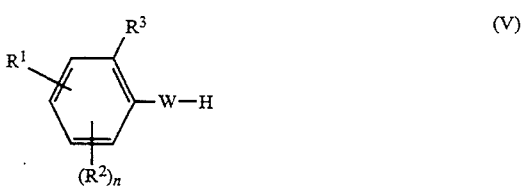

wherein $R^1$, $R^2$, $R^3$, W and n are each as defined above with the halide compound of the formula:

E—CH₂—CH₂—E  (VI)

Wherein E is as defined above.

The reaction of the (thio)phenol compound (V) and the halide compound (VI) to give the ethyl halide compound (VII) may be carried out usually in an inert solvent in the presence of a base at a temperature of from about 0° C. to the boiling point of the solvent, preferably from about a room temperature to the boiling point of the solvent.

The molar proportion of the (thio)phenol compound (V) and the halide compound (VI) to be used for the reaction is not limitative but is ordinary to be from about 1:1 to 1:10. The amount of the base to the (thio)phenol compound (V) is also limitative but it is preferably to be from about one to two equivalents.

Moreover, the amine compound (II) is produced by amination of the ethyl halide compound (VII) such as a method of reacting hydrazine with a phthalimide derivative obtained by reacting the ethyl halide compound (VII) with phthalimide.

The reaction of the ethyl halide compound (VII) and phthalimide to give the phthalimide derivative may be carried out usually in an inert solvent in the presence of a base at a temperature of from about 0° C. to the boiling temperature.

The molar proportion of the ethyl halide compound (VII) and phthalimide to be used for the reaction is not limitative but is ordinary to be from about 1:1 to 1:5. Examples of the inert solvent are alcohols (e.g. methanol, ethanol), aliphatic hydrocarbons (e.g. hexane, heptane), aromatic hydrocarbons (e.g. benzene, toluene, xylene), ethers (e.g. diethyl ether, diisopropyl ether, dioxane, tetrahydrofuran), ketons (e.g. acetone, methyl ethyl ketone, methyl isobutyl ketone), nitriles (e.g. acetonitrile, isobutylonitrile), acid amines (e.g. formamide, N,N-dimethylformamide, N,N-dimethylacetoamide), sulfur compounds (e.g. dimethyl sulfoxide, sulfolane), nitromethane, water and mixtures thereof.

The reaction of the phthalimide derivative and hydrazine to give the amine compound (II) may be carried out usually in an inert solvent at a temperature of from about 0° C. to the boiling temperature.

The molar proportion of the phthalimide derivative and hydrazine (or its hydrate) to be used for the reaction is not limitative but is ordinary to be from about 1:1 to 1:10. Examples of the inert solvent are alcohols (e.g. methanol, ethanol), aliphatic hydrocarbons (e.g. hexane, heptane), aromatic hydrocarbons (e.g. benzene, toluene, xylene), ethers (e.g. diethyl ether, diisopropyl ether, dioxane, tetrahydrofuran), acid amines (e.g. formamide, N,N-dimethylformamide, N,N-dimethylacetoamide), nitromethane, water and mixtures thereof.

The phthalimide derivative can be used with or without its purification in the above reaction.

Method (ii):

The amine compound (II) is produced by reducing the nitrile compound of the formula:

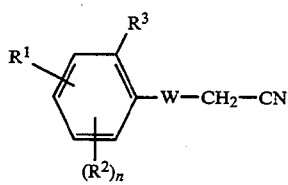   (VIII)

wherein $R^1$, $R^2$, $R^3$, W and n are each defined above. Furthermore, the nitrile compound (VIII) is produced by reacting the (thio)phenol compound (V) with chloroacetonitrile.

The reaction from the (thio)phenol compound (V) and chloroacetonitrile to the nitrile compound (VIII) may be carried out usually in an inert solvent in the presence of base at a temperature of from about 0° C. to the boiling point of the solvent, preferably from about a room temperature to the boiling point of the solvent.

The molar proportion of the (thio)phenol compound (V) and chloroacetonitrile to be used for the reaction is not limitative but is ordinary to be from about 1:1 to 1:5. The amount of the base to the (thio)phenol compound (V) is also not limitative but it is preferably to be from about one to five equivalents.

Moreover, the amine compound (II) is produced by reducing the nitrile compound (VIII) in the presence of a reducing reagent. Examples of the reducing reagent are boron hydride, aluminum hydride, lithium aluminum hydride, Raney nickel-hydrogen, palladium-hydrogen, platinum oxide-hydrogen, rhodium-alumina-hydrogen, etc.

The reaction conditions such as the solvent, the temperature and molar proportion of starting materials, etc. may vary within broad ranges depending upon the kind of the reducing reagent, but can be readily determined by a conventional manner.

Examples of the amide derivatives (I) of the present invention are shown in Table 1 and Table 2.

The amide derivatives (I) of the present invention have some asymmetric carbon atoms and can form optical isomers. Those optical isomers and their mixtures fall within the scope of the present invention.

TABLE 1

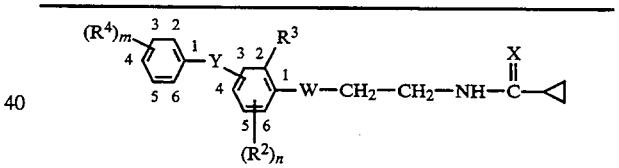

| (R²) n | R³ | (R⁴) m | Y | Substituted position of Y | W | X |
|---|---|---|---|---|---|---|
| H | Cl | H | O | 4 | O | O |
| H | Cl | 2-F | O | 4 | O | O |
| H | Cl | 3-F | O | 4 | O | O |
| H | Cl | 4-F | O | 4 | O | O |
| H | Cl | 2,4-F₂ | O | 4 | O | O |
| H | Cl | 3,5-F₂ | O | 4 | O | O |
| H | Cl | 3-Cl | O | 4 | O | O |
| H | Cl | 4-Cl | O | 4 | O | O |
| H | Cl | 3-Br | O | 4 | O | O |
| H | Cl | 3,5-Cl₂ | O | 4 | O | O |
| H | Cl | 3-CH₃ | O | 4 | O | O |
| H | Cl | 3-C₂H₅ | O | 4 | O | O |
| H | Cl | 3-n-C₃H₇ | O | 4 | O | O |
| H | Cl | 3-n-C₄H₉ | O | 4 | O | O |
| H | Cl | 3-iso-C₃H₇ | O | 4 | O | O |
| H | Cl | 3-CF₃ | O | 4 | O | O |
| H | Cl | 3-CF₂H | O | 4 | O | O |
| H | Cl | 3-C₂F₅ | O | 4 | O | O |
| H | Cl | H | O | 4 | O | S |
| H | Cl | 3-F | O | 4 | O | S |
| H | Cl | 4-F | O | 4 | O | S |
| H | Cl | 2,4-F₂ | O | 4 | O | S |
| H | Cl | 3,5-F | O | 4 | O | S |
| H | Cl | 3-CH₃ | O | 4 | O | S |
| H | Cl | 3-Cl | O | 4 | O | S |
| H | Cl | H | O | 4 | S | O |
| H | Cl | 3-F | O | 4 | S | O |
| H | Cl | 3,5-F₂ | O | 4 | S | O |
| H | Cl | 3-Cl | O | 4 | S | S |

TABLE 1-continued

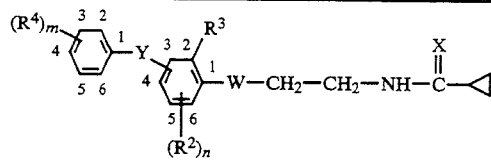

| (R²)n | R³ | (R⁴)m | Y | Substituted position of Y | W | X |
|---|---|---|---|---|---|---|
| H | Cl | 3-Cl | S | 4 | O | O |
| H | Cl | 3,5-F₂ | S | 4 | S | S |
| H | Cl | 3-Cl | S | 4 | S | O |
| H | Cl | H | O | 4 | O | O |
| 5-F | Cl | H | O | 4 | O | O |
| 5-Cl | Cl | 3,5-F₂ | O | 4 | O | O |
| 5-CH₃ | Cl | 3,5-F₂ | O | 4 | O | O |
| 6-F | Cl | 3,5-F₂ | O | 4 | O | O |
| 6-Cl | Cl | H | O | 4 | O | O |
| H | Cl | H | O | 5 | O | O |
| H | Cl | 3-F | O | 5 | O | O |
| H | Cl | 3,5-F₂ | O | 5 | O | O |
| H | Cl | 2,4-F₂ | O | 5 | O | O |
| H | Cl | 3-Cl | O | 5 | O | O |
| H | Cl | 3-CH₃ | O | 5 | O | O |
| 4-Cl | Cl | H | O | 5 | O | O |
| H | Cl | H | S | 5 | O | O |
| H | Cl | H | O | 5 | O | S |
| H | Cl | 3,5-F₂ | O | 5 | S | S |
| H | F | H | O | 4 | O | O |
| H | F | 3-F | O | 4 | O | O |
| H | F | 3,5-F₂ | O | 4 | O | O |
| H | F | 3-CH₃ | O | 4 | O | O |

TABLE 1-continued

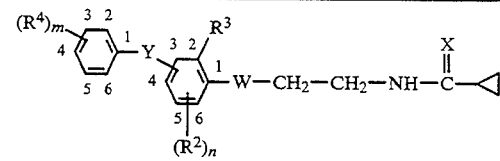

| (R²)n | R³ | (R⁴)m | Y | Substituted position of Y | W | X |
|---|---|---|---|---|---|---|
| H | F | 3,5-F₂ | O | 5 | O | O |
| H | F | 3,5-F₂ | O | 4 | O | S |
| H | CH₃ | H | O | 4 | O | O |
| H | CH₃ | 3-F | O | 4 | O | O |
| H | CH₃ | 3,5-F₂ | O | 4 | O | O |
| H | CH₃ | 3-Cl | O | 4 | O | O |
| H | CH₃ | 3-CH₃ | O | 4 | O | O |
| H | CH₃ | 3,5-F₂ | O | 4 | O | S |
| H | CH₃ | H | S | 4 | O | O |
| H | CH₃ | 3,5-F₂ | O | 5 | O | O |
| H | C₂H₅ | H | O | 4 | O | O |
| H | iso-C₃H₇ | H | O | 4 | O | O |
| H | Cl | H | CH₂ | 4 | O | O |
| 5-Cl | Cl | H | CH₂ | 4 | O | O |
| 5-CH₃ | Cl | H | CH₂ | 4 | O | O |
| 5-F | Cl | H | CH₂ | 4 | O | O |
| H | Cl | H | CH₂ | 4 | O | S |
| H | Cl | H | CH₂ | 5 | O | O |
| H | Cl | H | CH₂ | 5 | O | S |
| H | Cl | H | NH | 4 | O | O |
| H | F | H | CH₂ | 4 | O | O |
| H | CH₃ | H | CH₂ | 4 | O | O |
| H | Br | H | CH₂ | 4 | O | O |

TABLE 2

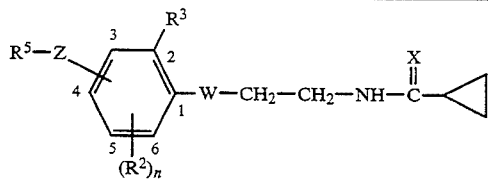

| (R²)n | R³ | R⁵ | Z | Substituted position of Z | W | X |
|---|---|---|---|---|---|---|
| H | Cl | CH(CH₃)C₂H₅ | O | 4 | O | O |
| H | Br | CH(CH₃)C₂H₅ | O | 4 | O | O |
| H | F | CH(CH₃)C₂H₅ | O | 4 | O | O |
| H | CH₃ | CH(CH₃)C₂H₅ | O | 4 | O | O |
| H | C₂H₅ | CH(CH₃)C₂H₅ | O | 4 | O | O |
| H | iso-C₃H₇ | CH(CH₃)C₂H₅ | O | 4 | O | O |
| 5-Cl | Cl | CH(CH₃)C₂H₅ | O | 4 | O | O |
| 5-F | Cl | CH(CH₃)C₂H₅ | O | 4 | O | O |
| 5-CH₃ | Cl | CH(CH₃)C₂H₅ | O | 4 | O | O |
| H | Cl | CH(CH₃)C₂H₅ | O | 4 | O | S |
| H | Cl | CH(CH₃)C₂H₅ | O | 4 | S | O |
| H | Cl | CH(CH₃)C₂H₅ | O | 4 | S | S |
| H | Cl | CH(C₂H₅)C₂H₅ | O | 4 | O | O |
| H | Cl | CH(C₂H₅)C₂H₅ | O | 4 | O | S |
| H | Cl | CH(CH₃)₂ | O | 4 | O | O |
| H | Cl | CH(CH₃)C₂H₅ | O | 5 | O | O |
| H | Cl | CH(CH₃)C₂H₅ | O | 5 | O | S |
| H | Cl | CH₂CH(CH₃)₂ | O | 4 | O | O |
| H | CH₃ | CH₂CH(CH₃)₂ | O | 4 | O | O |
| H | Cl | CH₂C(CH₃)₃ | O | 4 | O | O |
| H | Cl | CH₂CCl(CH₃)₂ | O | 4 | O | O |
| H | Cl | CH₂CCl(CH₃)₂ | O | 4 | O | S |
| H | Cl | CH₂CCl(CH₃)C₂H₅ | O | 4 | O | O |
| H | Cl | CH₂CH=C(CH₃)₂ | O | 4 | O | O |
| H | Cl | CH₂C(CH₃)=CH₂ | O | 4 | O | O |
| H | Cl | CH₂OCH₂CH(CH₃)₂ | — | 4 | O | O |
| H | Cl | CH₂OCH₂CH(CH₃)₂ | — | 4 | O | S |
| H | Cl | CH₂OCH₂CH(CH₃)₂ | — | 4 | S | O |
| H | Cl | CH₂OCH₂CH(CH₃)₂ | — | 4 | S | S |
| 5-Cl | Cl | CH₂OCH₂CH(CH₃)₂ | — | 4 | O | O |
| 5-F | Cl | CH₂OCH₂CH(CH₃)₂ | — | 4 | O | O |
| H | Cl | CH₂OCH₂CH(CH₃)₂ | — | 5 | O | O |
| H | Cl | CH₂OCH₂CH(CH₃)₂ | — | 5 | O | S |

TABLE 2-continued

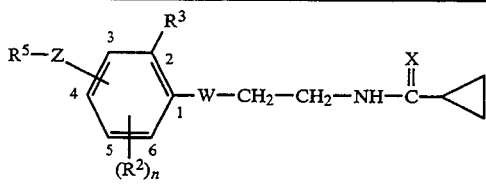

| (R²)n | R³ | R⁵ | Z | Substituted position of Z | W | X |
|---|---|---|---|---|---|---|
| H | Cl | CH(CH₃)(n-C₃H₇) | O | 4 | O | O |
| H | Cl | CH(CH₃)(n-C₄H₉) | O | 4 | O | O |
| H | Cl | CH(CH₃)(n-C₃H₇) | O | 4 | O | S |
| H | CH₃ | CH₂OCH₂CH(CH₃)₂ | — | 4 | O | O |
| H | F | CH₂OCH₂CH(CH₃)₂ | — | 4 | O | O |
| H | Cl | CH₂CH(CH₃)C₂H₅ | — | 4 | O | O |
| H | Cl | CH₂CH(CH₃)C₂H₅ | — | 4 | O | S |
| 5-Cl | Cl | CH₂CH(CH₃)C₂H₅ | — | 4 | O | O |
| H | Cl | CH₂CH(C₂H₅)C₂H₅ | — | 4 | O | O |
| H | Cl | CH₂CH(C₂H₅)C₂H₅ | — | 4 | O | S |
| H | Cl | CH₂CH(C₂H₅)C₂H₅ | — | 5 | O | O |
| H | Cl | CH₂CH(CH₃)C₂H₅ | O | 4 | O | O |
| 4-Cl | Cl | CH(CH₃)C₂H₅ | O | 5 | O | O |
| 4-F | F | CH(CH₃)C₂H₅ | O | 5 | O | O |
| H | Cl | cyclo-C₆H₁₁ | O | 4 | O | O |
| H | Cl | cyclo-C₆H₁₀(4-CH₃) | O | 4 | O | O |
| H | Cl | cyclo-C₆H₁₀(2-Cl) | O | 4 | O | O |
| H | Cl | cyclo-C₆H₁₁ | — | 4 | O | O |
| H | Cl | cyclo-C₃H₅CH₂ | O | 4 | O | O |
| H | Cl | cyclo-C₃H₅CH₂ | — | 4 | O | O |
| H | Cl | cyclo-C₆H₁₁CH₂ | — | 4 | O | O |
| H | Cl | cyclo-C₃H₄(1-CH₃)CH₂ | O | 4 | O | O |

Examples of the insect pests against which the amide derivatives (I) of the present invention exhibit controlling effects are as shown below.

Hemiptera:

Planthoppers such as brown planthopper (*Nilaparvata lugens*), white-backed rice planthopper (*Sogatella furcifera*) and small brown planthopper (*Laodelphax striatellus*); leafhoppers such as green rice leafhopper (*Nephotettix cincticeps*), *Nephotettix virescense*, *Nephotettix nigropictus*, zig-zag rice leafhopper (*Recilia dorsalis*), tea green leafhopper (*Empoasca onukii*) and grape leafhopper (*Arboridia apicalis*); aphids such as cotton aphid (*Aphis gossypii*) and green peach aphid (*Myzus persicae*); bugs; whiteflies (Aleyrodidae) such as sweet potato whitefly (*Bemisia tabaci*) and greenhouse whitefly (*Trialeurodes vaporariorum*); scales; mealy bugs; lace bugs (Tingidae); psyllids (Psyllidae), etc.

Lepidoptera:

Pyralid moths (Pyralidae) such as rice stem borer (*Chilo suppressalis*), rice leafroller (*Cnaphalocrocis medinalis*) and Indian meal moth (*Plodia interpunctella*); Noctuidae such as tobacco curworm (*Spodoptera litura*), rice armyworm (*Pseudaletia Separate*), cabbage armyworm (*Mamestra brassicae*) and beet semi-looper (*Autographa nigrisigna*); Agrothis spp. such as turnip cutworm (*Agrothis segetum*) and black cutworm (*Agrothis ipsilon*); Heliothis spp.; Pieridae such as common cabbageworm (*Pieris rapae crucivora*); tortricid moths (Tortricidae) such as Adoxophyes spp. and Grapholita spp.; Carposinidae such as lyonetiid moths (Lyonetiidae), leaf-blotch miners (Gracillariidae), gelechiid moths (Gelechiidae) and tussock moths (Lymantriidae); diamond-back moth (*Plutella Xylostella*), clothes moths (Tineidae), casemaking clothes moth (*Tinea translucens*) and webbing clothes moth (*Tineola bisselliella*), etc.

Diptera:

Mosquitos (Calicidae) such as common mosquito (*Culex pipiens pallens*) and Culex tritaeniorhynchus; Aedes spp. such as *Aedes aegypti* and *Aedes albopictus*; Anopheles spp. such as *Anopheles sinensis*; midges (Chironomidae); Muscidae such as housefly (*musca domestica*) and false stablefly (*Muscina stabulans*); Calliphoridae; Sarcophagidae; lesser housefly (*Fannia canicularis*); anthomyiid flies (Anthomyiidae) such as seedcorn maggot (*Delia platura*) and onion maggot (*Delia antique*); fruit flies (Tephritidae); shore flies (Ephydridae); small fruit flies (Drosophilidae); moth flies (Psychodidae); black flies (Simuliidae); Tabanidae; stable flies (Stomoxyidae); etc.

Coleoptera:

Leaf beetles (Chrysomelidae) such as cucurbit beetle (*Aulacophora femoralis*), striped flea beetles (*phyllotrata striolata*), western corn rootworm (*Diabrotica virgifora*) and southern corn root worm (*Diabrotica undecimpunctata*); scarabs (Scarabaeidae) such as cupreous chafer (*Anomala cuprea*) and soybeen beetle (*Anomala rufocuprea*); weevils (Cureulionidae) such as maize weevil (*Sitophilus zeamais*), rice water weevil (*Lissorhoptrus Oryzophilus*) and adzuki bean weevil (*Callosobruchys chineneis*), etc.; darkling beetles (Tenebrionidae) such as yellow mealworm (*Tenebrio moliter*) and red flour beetles (*Tribolium castaneum*); Anobiidae; Coccinellidae such as twenty-eight-spotted ladybirds (*Epilachna vigintioctopunctata*); powderpost beetles (Lyctidae); false powderpost beetles (Bostrychidae); Cerambysidae, etc.

Dictyoptera:

Blattellidae such as German cockroach (*Blattella germanica*); Blattidae such as smokybrown cockroach (*Periplaneta fuliginosa*), American cockroach (*Periplaneta americana*), brown cockroach (*Periplaneta brunnea*) and oriental cockroach (*Blatta orientalis*), etc.

Thysanoptera:

Thrips such as *Thrips palmi*, yellow tea thrips (*Scirtothrips dorsalis*) and flower thrips (*Thrips hawaiiensis*), etc.

Hymenoptera:

Ants (Formicidae); sawflies (Tenthredinidae) such as cabbage sawfly (*Athalia rosae ruficornis*), etc.

Orthoptera:

Mole crickets (Gryllotalpidae); grasshoppers (Acrididae), etc.

Aphaniptera:

*Purex irritans*, etc.

Anoplura:

*Pediculus humanus capitis, Phthirus pubis*, etc.

Isoptera:

*Reticulitermes speratus*, Formosan subterrauean termite (*Coptotermes formosanus*), etc.

Among the insect pests as above exemplified, the amide derivatives (I) are particularly effective in controlling those belonging to Hemiptera and also exhibit a remarkable controlling effect on planthoppers and leafhoppers in a field of rice plant or aphids.

The amide derivatives (I) may be used alone as insecticides or in mixtures with other insecticides and/or acaricides to enhance or expand their insecticidal or pesticidal use.

Examples of the other insecticides and/or acaricide include organophosphorus compounds (e.g. fenitrothion (O,O-dimethyl O-(3-methyl-4-nitrophenyl)phosphorothioate), fenthion (O,O-dimethyl O-[3-methyl-4-(methylthio)phenyl]phosphorothioate), diazinon (O,O-diethyl-O-(2-isopropyl-6-methyl-pyrimidin-4-yl)phosphorothioate), chlorpyrifos (O,O-diethyl-O-(3,5,6-trichloro-2-pyridyl)phosphorothioate), acephate (O,S-dimethyl acetylphosphoramidothioate), methidathion (S-2,3-dihydro-5-methoxy-2-oxo-1,3,4-thiadiazol-3-ylmethyl O,O-dimethylphosphorodithioate), disulfoton (O,O-diethyl S-2-ethylthioethyl phosphorothioate), DDVP (2,2-dichlorovinyldimethylphosphate), sulprofos (O-ethyl O-4-(methylthio)phenyl S-propyl phosphorodithioate), cyanophos (O-4-cyanophenyl O,O-dimethyl phosphorothioate), dioxabenzofos (2-methoxy-4H-1,3,2-benzodioxaphosphinine-2-sulphide), dimethoate (O,O-diethyl-S-(N-methylcarbamoylmethyl)dithiophosphate), phenthoate (ethyl 2-dimethoxyphosphinothioylthio(phenyl)acetate), malathion (diethyl (dimethoxyphosphinothioylthio)succinate), trichlorfon (dimethyl 2,2,2-trichloro-1-hydroxyethylphosphonate), azinphos-methyl (S-3,4-dihydro-4-oxo-1,2,3-benzotriazin-3-ylmethyl O,O-dimethylphosphoro-dithioate) and monocrotophos (dimethyl (E)-1-methyl-2-(methylcarbamoyl)vinyl phosphate), etc.); carbamate derivatives (e.g. BPMC (2-sec-butylphenyl methylcarbamate), benfuracarb (ethyl N-[2,3-dihydro-2,2-dimethylbenzofuran-7-yloxycarbonyl(methyl)aminothio]-N-isopropyl-beta-alanite), propoxur (2-isopropoxyephenyl N-methylcarbamate), carbosulfan (2,3-dihydro-2,2-dimethyl-7-benzo[b]furanyl N-methylcarbamate), carbaryl (1-naphthyl-N-methylcarbamate), methomyl (S-methyl-N-[(methylcarbamoyl)oxy]thioacetimidate, ethiofencarb (2-(ethylthiomethyl)phenyl methylcarbamate), aldicarb (2-methyl-2(methylthio)propionaldehyde O-methylcarbamoyloxime) and Oxamyl (N,N-dimethyl-2-methylcarbamoyloxyimino-2-(methylthio)acetamide), etc.); pyrethroides (e.g. ethofenprop (2-(4-ethoxyphenyl-2-methylpropyl-3-phenoxybenzylether), fenvalerate ((RS)-alpha-cyano-3-phenoxybenzyl (RS)-2-(4-chlorophenyl)-3-methylbutyrate), esfenvalerate ((S)-alpha-cyano-3-phenoxybenzyl (S)-2-(4-chlorophenyl)-3-methylbutyrate), fenpropathrin ((RS)-alpha-cyano-3-phenoxybenzyl 2,2,3,3-tetramethylcyclopropanecarboxylate), cypermethrin ((RS)-alpha-cyano-3-phenoxybenzyl (1RS,3RS)-(1RS,3RS)-3-(2,2-dichlorovinyl)-2,2-dimethylcyclopropanecarboxylate),- permethrin (3-phenoxybenzyl (1RS,3RS)-(1RS,3RS)-3-(2,2-dichlorovinyl)-2,2-dimethylcyclopropanecarboxylate), cyhalothrin ((R,S)-alpha-cyano-3-phenoxybenzyl (Z)-(1RS,3RS)-3-(2-chloro-3,3,3-trifluoropropenyl)-2,2-dimethylcyclopropanecarboxylate), deltamethrin ((S)-alpha-cyano-m-phenoxybenzyl (1R,3R)-3-(2,2-dibromovinyl)-2,2-dimethylcyclopropanecarboxylate) and cycloprothrin ((RS)-alpha-cyano-3-phenoxybenzyl (RS)-2,2-dichloro-1-(4-ethoxyphenyl)cyclopropanecarboxylate), etc.); thiadiazine derivatives (e.g. buprofezin (2-tert-butylimino-3-isopropyl-5-phenyl-1,3,5-triadiazin-4-one), etc.); nitroimidazolidine derivatives (e.g. imidacloprid (1-(6-chloro-3-pyridylmethyl)-N-nitroimidazolidin-2-ylideneamine), etc.); nereistoxin derivatives (e.g. cartap (S,S'-(2-dimethylaminotrimethylene) bis(thiocarbamate), thiocyclam (N,N-dimethyl-1,2,3-trithian-5-ylamine) and bensultap (S,S'-2-dimethylaminotrimethylene di(benzenethiosulphonate), etc.); halogenated hydrocarbons (e.g. endosulfan (6,7,8,9,10,10-hexachloro-1,5,5a,6,9,9a-hexahydro-6,9-methano-2,4,3-benzodioxathiepin-3-oxide) and gamma-BHC (1,2,3,4,5,6-hexachlorocyclohexane), etc.); benzoylphenylurea derivatives (e.g. chlorfluazuron (1-[3,5-dichloro-4-(3-chloro-5-trifluoromethylpyridin-2-yloxy)phehyl]-3-(2,6-difluorobenzoyl)urea), teflubenzuron (1-(3,5-dichloro-2,4-difluorophenyl)-3-(2,6-difluorobenzoyl)urea) and flufenoxuron (1-[4-(2-chloro-4-trifluoromethylphenoxy)-2-fluorophenyl]-3-(2,6-difluorobenzoyl)urea, etc.); formamidine derivatives (e.g. amitraz (N,N'-[(methylimino)dimethylidyne]-di-2,4-xylidine) and chlordimeform (N'-(4-chloro-2-methylphenyl)-N,N-dimethylmethanimidamide), etc.).

On the practical use of the amide derivatives (I) as insecticides, they may be employed as such but are normally mixed with appropriate additives such as solid carriers, liquid carriers, gaseous carriers, feed, etc. to formulate their compositions. When desired or necessary, surfactants and other adjuvants may be further incorporated therein. The compositions may be prepared into any conventional forms such as oil sprays, emulsifiable concentrates, wettable powders, flowable concentrates (e.g. water-based suspension formulations, water-based emulsion formulations), granules, dusts, aerosals, heating smoking formulations (e.g. self-burning-type smoking formulations, chemical reaction-type smoking formulations, porous ceramic plate-type smoking formulations), ULV formulations, poison baits, etc.

The composition of the present invention contains generally the amide derivative(s) (I) as the active ingredient in an amount of from about 0.001% to 95% by weight based on the composition.

Examples of the solid carrier usable for making the composition are fine powders or granules of clays (e.g. kaolin clay, diatomaceous earth, synthetic hydrated silica, bentonite, Fubasami clay, terra alba), talc, ceramics, other inorganic minerals (e.g. sericite, quartz, sulfur, activated carbon, calcium carbonate, hydrated silica), chemical fertilizers (e.g. ammonium sulfate, ammonium phosphate, ammonium nitrate, urea, ammonium chloride), etc. Examples of the liquid carrier include water, alcohols (e.g. methanol, ethanol), ketones (e.g. acetone, methyl ethyl ketone), aromatic hydrocarbons (e.g. benzene, toluene, xylene, ethylbenzene, methylnaphthalene), aliphatic hydrocarbons (e.g. hexane, cyclohexane, kerosene, gas oil), esters (e.g. ethyl acetate, butyl acetate), nitriles (e.g. acetonitriles, isobutyronitrile), ethers (e.g. diisopropyl ether, dioxane), acid amides (e.g. N,N-dimethylformamide, N,N-dimethylacetamide), halogenated hydrocarbons (e.g. dichloromethane, trichloroethane, carbon tetrachloride), dimethylsulfoxide, vegetable oils (e.g. soybean oil, cotton seed oil), etc. Examples of the gaseous carrier, i.e. a propellant, include freon gas, butane gas, LPG (liquefied petroleum gas), dimethyl ether, carbon dioxide, etc.

Examples of the surfactant are alkylsulfates, alkylsulfonates, alkylarylsulfonates, alkyl aryl ethers and polyoxyethylene derivatives thereof, polyethylene glycol ethers, polyvalent alcohol esters, sugar alcohol derivatives, etc. Examples of the adjuvants such as binders and dispersing agents are casein, gelatin, polysaccharides (e.g. starch powders, gum arabic, cellulose derivatives, alginic acid), lignin derivatives, bentonite, sugars, synthetic water-soluble high molecular weight substances (e.g. polyacrylic alcohol, polyvinylpyrrolidone, polyacrylic acid), etc. Examples of the stabilizer include PAP (acidic isopropyl phosphate), BHT (2,6-di-tert-butyl-4-methylphenol), BHA (mixture of 2-tert-butyl-4-methoxyphenol and 3-tert-butyl-4-methoxyphenol), vegetable oils, mineral oils, surfactants, fatty acids or esters thereof, etc.

The base material for self-burning-type smoking formulations may include, for example, burning heat-generating agents such as nitrates, nitrites, guanidine salts, potassium chlorate, nitrocellulose, ethyl cellulose and wood powders, pyrolysis-promoting agents such as alkali metal salts, alkaline earth metal salts, dichromates and chromates, oxygen-supplying agents such as potassium nitrate, burning-supporting agents such as melamine and wheat starch, extenders such as diatomaceous earth, binders such as synthetic pastes, etc. The base material for chemical reaction-type smoking formulations can include, for example, heat-generating agents such as alkali metal sulfides, alkali metal polysulfides, alkali metal hydrosulfides, hydrated salts of alkali metals and calcium oxide, catalyzing agents such as carbonaceous substances, iron carbide and activated clay, organic foaming agents such as azodicarbonamide, benzenesulfonyl hydrazides, dinitrosopentamethylenetetramine, polystyrene and polyurethane, fillers such as natural fiber pieces and synthetic fiber pieces, etc. The base material for poison baits may contain feed components such as crop powders, essential vegetable oil, sugars and crystalline cellulose, antioxidants such as dibutylhydroxytoluene and nordihydroguaiaretic acid, preservatives such as dehydroacetic acid, feeding error preventing agents such as red paper powders, incentive flavors such as cheese flavor and onion flavor, etc.

Flowable concentrates (water-based suspension or emulsion formulations) are generally obtained by dispersing about 1 to 75 parts by weight of the amide derivative (I) as the active ingredient finely and uniformly into water containing about 0.5 to 15 parts by weight of a dispersing agent, about 0.1 to 10 parts by weight of a suspending agent (e.g. protective colloids, compounds giving a thixotropic property) and optionally about 0 to 10 parts by weight of an auxiliary agent(s) such as a defoaming agent, an anticorrosive agent, a stabilizing agent, a spreading agents, penetration auxiliaries, antifreezing agent, an antibacterial agent, an antimolding agent and the like. The use of an oil, into which the active ingredient is hardly soluble, in place of water affords oil-based suspension formulations. Examples of the protective colloids as above mentioned are gelatin, casein, gums, cellulose ethers, polyvinyl alcohol, etc.

Examples of the compounds giving a thixotropic property are bentonite, aluminum magnesium silicate, xanthane gum, polyacrylic acid, etc.

The composition of the present invention thus obtained may be used as such or after diluting with water. It may be also used in a mixture with any other active component or composition chosen from insecticides, nematocides, acaricides, fungicides, bacteriocides, herbicides, plant growth regulators, synergistic agents, fertilizers, soil conditioners, animal feed, etc. Alternatively, the composition of the invention may be applied separately but simultaneously with said other active component or composition.

For the purpose of controlling insect pests in the agricultural field, the amide derivative (I) according to the present invention may be applied to the insect pests or the locus where the insect pests propagate generally in an amount of about 0.001 g to 500 g, and preferably about 0.1 g to 500 g per 10 ares. when the amide derivative (I) is applied in a form of emulsifiable concentrate, wettable powder, flowable concentrate or the like after dilution with water, its concentration may be from about 0.0001 to 1000 ppm. Granules, dusts, etc. may be used as such, i.e. without water dilution. When the amide derivative (I) is used for household or public hygiene, it may be used in the form of emulsifiable concentrate, wettable powder, flowable concentrate or the like with water dilution, etc. In this case, the concentration of the active ingredient may be from about 0.0001 to 10,000 ppm. In case of oils, aerosol, fumigants, ULV formulations, poison baits, etc., they may be applied as such. However, the doses and concentrations may vary within broad ranges depending upon the composition, the application time, the place applied, the application method, the kind of insect pests, the condition of damage, etc. and may be increased or decreased, irrespective of the general ranges set forth above.

Practical and presently preferred embodiments of the invention will be hereinafter explained in more detail referring to Production Examples, Formulation Examples and Test Examples. These examples, however, should not be construed to be limitative.

In the following Production Examples, % is by weight unless otherwise indicated.

PRODUCTION EXAMPLE 1

(Production Of Compound No. 1)

To a mixture of 200 g (0.667 mol) of 2-[2-chloro-4-(3,5-difluorophenoxy)phenoxy]ethylamine, 81 g (0.80 mol) of triethylamine and 8 liter of toluene, there was added dropwise a solution of 70 g (0.67 mol) of cyclopropane carbonylchloride in 2 liter of toluene with stirring at a temperature of from 5° C. to 10° C. After 2 hours, the reaction mixture was stirred at a room temperature for 15 hours. After the reaction was completed, the resultant mixture was washed twice with water, dried over anhydrous magnesium sulfate and concentrated under reduced pressure. The residue was subjected to silica gel chromatography to give 163 g of N-{2-[2-chloro-4-(3,5-difluorophenoxy)phenoxy]ethyl}-cyclopropane carboxyamide as a white crystal (m.p. 89°–90° C.).

PRODUCTION EXAMPLE 2

(Production of Compound No. 2)

To a mixture of 230 g (0.667 mol) of 2-[2-bromo-4-(3,5-difluorophenoxy)phenoxy]ethylamine, 81 g (0.80 mol) of triethylamine and 8 liter of toluene, there is added dropwise a solution of 70 g (0.67 mol) of cyclopropane carbonyl chloride in 2 liter of toluene with stirring at a temperature of from 5° C. to 10° C. After 2 hours, the reaction mixture is stirred at a room temperature for 15 hours. After the reaction is completed, the resultant mixture is washed twice with water, dried over anhydrous magnesium sulfate and concentrated under reduced pressure. The residue is subjected to silica gel chromatography to give N-{2-[2-bromo-4-(3,5-difluorophenoxy)phenoxy]ethyl}-cyclopropane carboxyamide.

PRODUCTION EXAMPLE 3

(Production of Compound No. 9)

To a mixture of 185 g (0.667 mol) of 2-[2-chloro-4-(3-tolyloxy)phenoxy]ethylamine, 81 g (0.80 mol) of triethylamine and 8 liter of toluene, there is added dropwise a solution of 70 g (0.67 mol) of cyclopropane carbonyl chloride in 2 liter of toluene with stirring at a temperature of from 5° C. to 10° C. After 2 hours, the reaction mixture is stirred at a room temperature for 15 hours. After the reaction is completed, the resultant mixture is washed twice with water, dried over anhydrous magnesium sulfate and concentrated under reduced pressure. The residue is subjected to silica gel chromatography to give N-{2-[2-chloro-4-(3-tolyloxy)phenoxy]ethyl}-cyclopropane carboxyamide.

PRODUCTION EXAMPLE 4

(Production of Compound No. 17)

To a mixture of 162 g (0.667 mol) of 2-(2-chloro-4-propoxymethylphenoxy)ethylamine, 81 g (0.80 mol) of triethylamine and 8 liter of toluene, there is added dropwise a solution of 70 g (0.67 mol) of cyclopropane carbonyl chloride in 2 liter of toluene with stirring at a temperature of from 5° C. to 10° C. After 2 hours, the reaction mixture is stirred at a room temperature for 15 hours. After the reaction is completed, the resultant mixture is washed twice with water, dried over anhydrous magnesium sulfate and concentrated under reduced pressure. The residue is subjected to silica gel chromatography to give N-[2-(2-chloro-4-propoxymethylphenoxy)ethyl]-cyclopropane carboxyamide.

PRODUCTION EXAMPLE 5

(Production of compound No. 18)

To a mixture of 181 g (0.667 mol) of 2-[2-chloro-4-(2-methylbutoxymethyl)phenoxy]ethylamine, 81 g (0.80 mol) of triethylamine and 8 liter of toluene, there is added dropwise a solution of 70 g (0.67 mol) of cyclopropane carbonyl chloride in 2 liter of toluene with stirring at a temperature of from 5° C. to 10° C. After 2 hours, the reaction mixture is stirred at a room temperature for 15 hours. After the reaction is completed, the resultant mixture is washed twice with water, dried over anhydrous magnesium sulfate and concentrated under reduced pressure. The residue is subjected to silica gel chromatography to give N-{2-[2-chloro-4-(2-methylbutoxymethyl)phenoxy]ethyl}-cyclopropane carboxyamide.

PRODUCTION EXAMPLE 6

(Production of Compound Nos. 11, 19, 20, 21, 22, 23)

In the same procedure with the same molar proportion of materials as production example 1, N-2-[2-chloro-4-(1-methylpropoxy)phenoxy]ethyl-cyclopropane carboxyamide is obtained by using 2-[2-chloro-4-(1-methylpropoxy)phenoxy]ethylamine instead of 2-[2-chloro-4-(3,5-difluorophenoxy)phenoxy]ethylamine. In the same way, N-{2-[2-chloro-4-(4-trifluoromethylphenoxy)phenoxy]ethyl}-cyclopropane carboxyamide, N-{2-[2-chloro-4-(1-methyethoxy)phenoxy]ethyl}-cyclopropane carboxyamide, N-[2-(2-chloro-4-heptylphenoxy)ethyl]-cyclopropane carboxyamide, N-[2-(2-chloro-4-cyclohexyloxyphenyl)ethyl]-cyclopropane carboxyamide or N-{2-[2,5-dichloro-4-(3,5-difluorophenoxy)phenoxy]ethyl}-cyclopropane carboxyamide is obtained by using 2-[2-chloro-4-(4-trifluoromethyl)-phenoxy]ethylamine, 2-[2-chloro-4-(1-methylethoxy)-phenoxy]ethylamine, 2-(2-chloro-4-heptylphenoxy)ethylamine, 2-(2-chloro-4-cyclohexyloxyphenoxy)ethylamine or 2-[2,5-dichloro-4-(3,5-diflurophenoxy)-phenoxy]ethylamine.

PRODUCTION EXAMPLE 7

(Production of Compound Nos. 3)

A mixture of 500 mg (1.52 mmol) of N-[2-(4-benzyl-2-chlorophenoxy)ethyl]-cyclopropane carboxyamide, 614 mg (1.52 mmol) of a Lawesson's reagent and 20 ml of anhydrous toluene was refluxed by heating with stirring. After 20 minutes, the reaction mixture was cooled and concentrated under reduced pressure. The residue was subjected to silica gel chromatography to give 487 mg of N-[2-(4-benzyl-2-chlorophenoxy)ethyl]-cyclopropane thiocarboxyamide as a colorless oily substance $n_D^{23.6}$ 1.6041). After one week, the oily substance caked as a white solid (m.p. 90°–92° C. .

PRODUCTION EXAMPLE 8

(Production of Compounds Nos. 4, 16)

In the same procedure with the same molar proportion of materials as production example 7, N-{2-[2-chloro-4-(3,5-difluorophenoxy)phenoxy]ethyl}-cyclopropane thiocarboxyamide is obtained by using N-{2-[2-chloro-4-(3,5-difluorophenoxy)phenoxy]ethyl}-cyclopropane carboxyamide instead of N-[2-(4-benzyl-2-chlorophenoxy)ethyl]-cyclopropane carboxyamide. In the same way, N-{2-[2-chloro-4-(3-chlorophenoxy)-phenoxy]ethyl}-cyclopropane thiocarboxyamide is obtained by using N-{2-[2-chloro-4-(3-chlorophenoxy)-phenoxy]ethyl}-cyclopropane carboxyamide.

The compound numbers of the amide derivatives (I) are shown below. Some examples of the amide derivatives (I) as produced in the same manner as above are also included.

(1) N-{2-[2-Chloro-4-(3,5-difluorophenoxy)phenoxy]ethyl}-cyclopropane carboxyamide m.p. 89°–90° C.

(2) N-{2-[2-Bromo-4-(3,5-difluorophenoxy)phenoxy]ethyl}-cyclopropane carboxyamide (3 ) N-[2-(4-Benzyl-2-chlorophenoxy)ethyl]-cyclopropane thiocarboxyamide m.p. 90°–92° C.

(4) N-{2-[2-Chloro-4-(3,5-difluorophenoxy)phenoxy]ethyl}-cyclopropane thiocarboxyamide (5) N-{2-[2-Chloro-4-(3-fluorophenoxy)phenoxy]ethyl}-cyclopropane carboxyamide m.p. 75°–76° C.

(6) N-{2-[2-Chloro-4-(3-chlorophenoxy)phenoxy]ethyl}-cyclopropane carboxyamide m.p. 83.8° C.

(7) N-{2-[2-Chloro-4-(2,4-difluorophenoxy)phenoxy]ethyl}-cyclopropane carboxyamide m.p. 76°–77° C.

(8) N-[2-(2-Chloro-5-phenoxyphenoxy)ethyl]-cyclopropane carboxyamide m.p. 123°–124° C.
(9) N-{2-[2-Chloro-4-(3-tolyloxy)phenoxy]ethyl}-cyclopropane carboxyamide
(10) N-{2-[2-Chloro-4-(2-methylpropoxymethyl)phenoxy]ethyl}-cyclopropane carboxyamide m.p. 50°–51° C.
(11) N-{2-[2-Chloro-4-(1-methylpropoxy)phenoxy]ethyl}-cyclopropane thiocarboxyamide
(12) N-{2-[2-Chloro-4-(2-ethylbutyl)phenoxy]ethyl}-cyclopropane carboxyamide m.p. 56°–57° C.
(13) N-[2-(4-Benzyl-2-chlorophenoxy)ethyl]-cyclopropane carboxyamide m.p. 91°–92° C.
(14) N-{2-[2-Chloro-4-(1-methylpropoxy)phenoxy]ethyl}-cyclopropane carboxyamide $n_D^{22.2}$ 1.5344
(15) N-[2-(2-Chloro-4-phenoxyphenoxy)ethyl]-cyclopropane carboxyamide m.p. 95.5° C.
(16) N-{2-[2-Chloro-4-(3-chlorophenoxy)phenoxy]ethyl}-cyclopropane thiocarboxyamide
(17) N-[2-(2-Chloro-4-propoxymethylphenoxy)ethyl]-cyclopropane carboxyamide
(18) N-{2-[2-Chloro-4-(2-methylbutoxymethyl)phenoxy]ethyl}-cyclopropane carboxyamide
(19) N-{2-[2-Chloro-4-(4-trifluoromethylphenoxy)phenoxy]ethyl}-cyclopropane carboxyamide
(20) N-{2-[2-Chloro-4-(1-methylethoxy)phenoxy]ethyl}-cyclopropane carboxyamide
(21) N-[2-(2-Chloro-4-heptylphenoxy)ethyl]-cyclopropane carboxyamide
(22) N-[2-(2-Chloro-4-cyclohexyloxyphenoxy)ethyl]-cyclopropane carboxyamide
(23) N-{2-[2,5-Dichloro-4-(3,5-difluorophenoxy)phenoxy]ethyl}-cyclopropane carboxyamide Some examples for production of intermediary compounds are shown below.

PRODUCTION EXAMPLE 9

(Production of Intermediary Compound No. 104)

A mixture of 14.99 g of 2-chloro-4-(3-chlorophenoxy)phenol, 4.44 g of chloro acetonitrile and 8.94 g of potassium carbonate in 150 ml dimethylformamide was stirred at a temperature of 70° to 80° C. in an oil bath for 5 hours. The reaction mixture was cooled to room temperature, poured into water and extracted twice with 100 ml of ethyl acetate. The extracts were combined together, washed twice with 200 ml of water, dried over anhydrous magnesium sulfate and concentrated under reduced pressure to give 14.0 g of [2-Chloro-4-(3-chlorophenoxy)phenoxy]acetonitrile as a crude product.

A solution of 14.0 g of the crude product as above obtained in 200 ml of tetrahydrofuran was kept at 0° C., and 200 ml of borane-tetrahydrofuran complex (1.0M tetrahydrofuran solution) were dropwise added thereto with stirring at a temperature of 0° to 5° C. The resultant mixture was stirred at room temperature overnight and then poured into 300 ml of water, followed by removal of tetrahydrofuran by distillation under reduced pressure. The reaction product was salted out and extracted three times with 100 ml of ethyl acetate. The extracts were combined together, washed with 200 ml each of a 5% aqueous solution of hydrochloric acid, water and a 10% aqueous solution of sodium hydroxide, dried over anhydrous magnesium sulfate and concentrated under reduced pressure to give 11.4 g of 2-[2-Chloro-4-(3-chlorophenoxy)phenoxy]ethylamine. Yield: 65%. $n_D^{24.3}$: 1.5842.

In the same manner as above, the following compounds are obtained.

(101) 2-(2-Chloro-4-phenoxyphenoxy)ethylamine $n_D^{24.3}$: 1.5991
(102) 2-(2-Chloro-4-benzylphenoxy)ethylamine $n_D^{24.3}$: 1.5851
(103) 2-[2-Chloro-4-(3,5-difluorophenoxy)phenoxy]ethylamine $n_D^{24.3}$: 1.5620
(104) 2-[2-Chloro-4-(3-chlorophenoxy)phenoxy]ethylamine $n_D^{24.3}$: 1.5842
(105) 2-[2-Chloro-4-(3-fluorophenoxy)phenoxy]ethylamine $n_D^{24.3}$: 1.5769
(106) 2-[2-Chloro-4-(3-methylphenoxy)phenoxy]ethylamine $n_D^{24.3}$: 1.5842
(107) 2-[2-Chloro-4-(3-trifluoromethoxyphenoxy)phenoxy]ethylamine
(108) 2-[2-Chloro-4-(2,4-difluorophenoxy)phenoxy]ethylamine $n_D^{24.3}$: 1.5599
(110) 2-[2-Chloro-4-(3,4-dichlorobenzyl)phenoxy]ethylamine $n_D^{24.8}$: 1.5921
(111) 2-[2-Chloro-4-(3,5-difluorobenzyl)phenoxy]ethylamine $n_D^{24.8}$: 1.5761
(112) 2-[2,5-Dichloro-4-(3,5-difluorophenoxy)phenoxy]ethylamine $n_D^{23}$: 1.5644
(113) 2-[2,6-Dichloro-4-(3,5-difluorophenoxy)phenoxy]ethylamine $n_D^{23}$: 1.5737
(114) 2-[2-Chloro-4-(3-bromophenoxy)phenoxy]ethylamine
(115) 2-[2-Chloro-5-(3,4-dichlorophenoxy)phenoxy]ethylamine $n_D^{23}$: 1.5624
(116) 2-[2-Chloro-5-(3,5-difluorophenoxy)phenoxy]ethylamine $n_D^{23}$: 1.5884
(117) 2-[2-Chloro-4-(4-fluorophenoxy)phenoxy]ethylamine $n_D^{25}$: 1.5721
(118) 2-[2-Chloro-4-(4-chlorophenoxy)phenoxy]ethylamine $n_D^{25}$: 1.5693
(119) 2-[2-Chloro-4-(4-trifluoromethylphenoxy)phenoxy]ethylamine
(120) 2-(2-Chloro-5-phenoxyphenoxy)ethylamine $n_D^{24.3}$: 1.5903

In Formulation Examples as set forth below, parts and % are all by weight. The compound numbers correspond to those in Production Examples.

Formulation Example 1 (Emulsifiable Concentrate)

To a solution of 10 parts of each of Compounds Nos. 1 to 23 in 35 parts of xylene and 35 parts of dimethylformamide, 14 parts of polyoxyethylene styrylphenyl ether and 6 parts of calcium dodecylbenzenesulfonate are added, and the resultant mixture is thoroughly mixed while stirring to give an emulsifiable concentrate containing the active ingredient in 10%.

Formulation Example 2 (Wettable Powder)

Twenty parts of each of Compounds Nos. 1 to 23 are added to a mixture of 4 parts of sodium laurylsulfate, 2 parts of calcium ligninsulfonate, 20 parts of fine powders of synthetic hydrated silica and 54 parts of diatomaceous earth, and the resultant mixture is stirred in a mixer to give a wettable powder containing the active ingredient in 20%.

Formulation Example 3 (Granules)

Five parts of sodium dodecylbenzenesulfonate, 30 parts of bentonite and 60 parts of clay are added to 5 parts of each of Compound No. 14 and the resultant mixture is pulverized and kneaded with a suitable amount of water. The mixture is granulated in a granulator and air-dried to give granules containing the active ingredient in 5%.

Formulation Example 4 (Granules)

Five parts of fine powder of synthetic hydrated silica, 5 parts of sodium dodecylbenzenesulfonate, 30 parts of bentonite and 55 parts of clay are added to 5 parts of each of Compound Nos. 1, 3, 5, 6, 7, 8, 10, 12, 13 and 15 and the resultant mixture is pulverized and kneaded with a suitable amount of water. The mixture is granulated in a granulator and air-dried to give granules containing the active ingredient in 5%.

Formulation Example 5 (Dusts)

To a mixture of 1 part of fine powders of synthetic hydrated silica, 1 part of an aggregating agent ("Driless B" manufactured by Sankyo Co., Ltd.) and 7.7 parts of clay, 0.3 part of each of Compound No. 14 is added, and the resultant mixture is well pestled in a mortar and further stirred in a mixer. To the thus obtained mixture, there are added 90 parts of cut clay, followed by mixing to give dusts containing the active ingredient in 0.3%.

Formulation Example 6 (Dusts)

A mixture of 0.3 part of each of Compound Nos. 1, 3, 5, 6, 7, 8, 10, 12, 13 and 15 and 0.03 part of fine powders of synthetic hydrated silica is stirred well in a mixer and pulverized by the aid of a centrifugal pulverizer. to the resultant mixture, 0.97 part of fine powers of synthetic hydrated silica, 1 part of "Driless B" and 7.7 parts of clay are added, and the resulting mixture is pestled in a mortar and stirred in a mixer. Ninety parts of cut clay are added thereto, and further mixing is effected in a sack to give dusts containing the active ingredient in 0.3%.

Formulation Example 7 (Dusts)

A mixture of 0.3 part of each of Compound No. 14, 2 parts of fenitrothion (O,O-dimethyl O-(3-methyl-4-nitrophenyl)phosphorothioate as an organo-phosphorus insecticide, 3 parts of fine powders of synthetic hydrated silica, 1 part of "Driless B" and 3.7 parts of clay are pestled in a mortar and stirred in a mixer. Then, 90 parts of cut clay are added thereto, and the resultant mixture is further mixed in a sack to give dusts.

Formulation Example 8 (Dusts)

A mixture of 0.3 part of each of Compound Nos. 1, 3, 5, 6, 7, 8, 10, 12, 13 and 15 and 0.03 part of fine powders of synthetic hydrated silica is stirred in a mixer and pulverized by a centrifugal pulverizer. After addition of 2 parts of fenitrothion, 2.97 parts of fine powders of synthetic hydrated silica, 1 part of "Driless B" and 3.7 parts of clay thereto, the resultant mixture is pestled in a mortar and stirred in a mixer. Then, 90 parts of cut clay are added thereto, and the resultant mixture is further mixed in a sack to give dusts.

Formulation Example 9 (Dusts)

A mixture of 0.3 part of each of Compound No. 14, 2 parts of BPMC (O-sec-butylphenyl N-methylcarbamate) as a carbamate insecticide, 3 parts of fine powders of synthetic hydrated silica, 1 part of "Driless B" and 3.7 parts of clay are pestled in a mortar and stirred in a mixer. Then, 90 parts of cut clay are added thereto, and the resultant mixture is further mixed in a sack to give dusts.

Formulation Example 10 (Dusts)

A mixture of 0.3 part of each of Compound Nos. 1, 3, 5, 6, 7, 8, 10, 12, 13 and 15 and 0.03 part of fine powders of synthetic hydrated silica is stirred in a mixer and pulverized by a centrifugal pulverizer. After addition of 2 parts of BPMC, 2.97 parts of fine powders of synthetic hydrated silica, 1 part of "Driless B" and 3.7 parts of clay thereto, the resultant mixture is pestled in a mortar and stirred in a mixer. Then, 90 parts of cut clay are added thereto, and the resultant mixture is further mixed in a sack to give dusts.

Formulation Example 11 (Dusts)

To a solution of 1 part of each of Compound Nos. 1 to 23 in an appropriate amount of acetone, 5 parts of fine powders of synthetic hydrated silica, 0.3 part of PAP (acidic isopropyl phosphate) and 93.7 parts of clay are added, and the resultant mixture is stirred in a mixer, followed by evaporation of acetone to give dusts containing the active ingredient in 1%.

Formulation Example 12 (Flowable Concentrate)

To 40 parts of an aqueous solution containing 2 parts of polyvinyl alcohol, 10 parts of each of Compound No. 14 are added, and the resultant mixture is stirred in a mixer. To the thus obtained dispersion, 40 parts of an aqueous solution containing 0.05 part of xanthane gum and 0.1 part of aluminum magnesium silicate are added, followed by addition of 10 parts of propylene glycol. The mixture is gently stirred to give a flowable concentrate containing the active ingredient in 10%.

Formulation Example 13 (Flowable Concentrate)

To 28.5 parts of an aqueous solution containing 2 parts of polyvinyl alcohol, 20 parts of each of Compound Nos. 1, 3, 5, 6, 7, 8, 10, 12, 13 and 15 and 1.5 parts of sorbitan trioleate are added, and the resultant mixture is finely pulverized by the aid a sand grinder to give particles of less than 3 microns in average particle size. To the resultant mixture, 40 parts of an aqueous solution containing 0.05 part of xanthane gum and 0.1 part of aluminum magnesium silicate are added, followed by addition of 10 parts of propylene glycol. The mixture is gently stirred to give a flowable concentrate containing the active ingredient in 20%.

Formulation Example 14 (Oil Spray)

Into a mixture of 5 parts of xylene and 5 parts of trichloroethane, 0.1 part of each of Compound Nos. 1 to 23 is dissolved, and the resultant solution is mixed with 89.9 parts of deodorized kerosene to give an oil spray containing the active ingredient in 0.1%.

Formulation Example 15 (Oil-Based Aerosol)

A solution of 0.1 part of each of Compound Nos. 1 to 23, 0.2 part of tetramethrin (2,2-dimethyl-3-(2-methyl-1-propenyl)cyclopropanecarboxylic acid (1,2,3,4,5,7-hexahydro-1,3-dioxo-2H-isoindol-2-yl)methyl ester) and 0.1 part of d-phenothrin (2,2-dimethyl-3-(2-methyl-1-propenyl)cyclopropanecarboxylic acid (3-phenoxyphenyl)methyl ester) in a mixture of 10 parts of trichloroethane and 59.6 parts of deodorized kerosene is filled in an aerosol container. After provision of a valve, 30 parts of a propellant (liquefied petroleum gas) is filled through the valve under compression to give an oil-based aerosol.

Formulation Example 16 (Water-Based Aerosol)

A solution of 0.2 part of each of Compound Nos. 1 to 23, 0.2 part of d-allethrin ((2,2-dimethyl-3-(2-methyl-1-propenyl)cyclopropanecarboxylic acid 2-methyl-4-oxo-3-(2-propenyl)-2-cyclopenten-2-yl ester), 0.2 part of d-phenothrin, 5 parts of xylene, 3.4 parts of deodorized kerosene and 1 part of an emulsifier ("ATMOS 300"$^R$, Atlas Chemical Co., Ltd.) in 50 parts of distilled water is filled in an aerosol container. After provision of a valve, 40 parts of a propellant (liquefied petroleum gas) is filled through the valve under compression to give a water-based aerosol.

Formulation Example 17 (Fumigant)

Each of Compound Nos. 1 to 23 (100 mg) is dissolved in an appropriate amount of acetone, and the resultant solution is impregnated with a porous ceramic plate (4.0×4.0×1.2 cm) to give a fumigant.

The following Test Examples show some of test results which support the controlling effect of the amide derivatives (I) on insect pests. The compound numbers correspond to those as shown in Production Examples. The compounds used for comparison are as follows:

| Compound symbol | Chemical structure | Remarks |
|---|---|---|
| A | 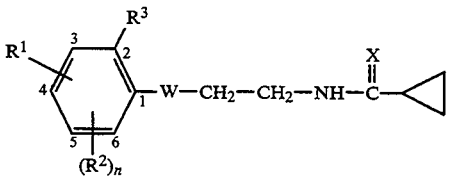 | Compound disclosed in U.S. Pat. No. 4,859,706 |

Test Example 1

Metamorphosis inhibitory activity against brown rice planthopper nymphs:

An emulsifiable concentrate prepared according to Formulation Example 1 was diluted with water to make a predetermined concentration. The dilution was sprayed onto rice plants cultivated in polyethylene cups at a rate of 20 ml/2 pots on a turning table. After air-drying, the plants were infested with about ten 3rd instar nymphs of brown rice planthopper (*Nilaparvata lugens*). After 10 days, the number of normal adults was counted to obtain an emergence inhibitory rate. The results are shown in Table 3.

TABLE 3

| Compound No. | Concentration (ppm) | Inhibitory rate (%) |
|---|---|---|
| 1 | 5 | 100 |
|   | 0.05 | 100 |
| 3 | 5 | 100 |
|   | 0.05 | 100 |
| 4 | 5 | 100 |
|   | 0.05 | 100 |
| 5 | 5 | 100 |
|   | 0.05 | 100 |
| 6 | 5 | 100 |
|   | 0.05 | 100 |
| 7 | 5 | 100 |
| 8 | 5 | 100 |
|   | 0.05 | 100 |
| 10 | 5 | 100 |
|   | 0.05 | 100 |
| 11 | 5 | 100 |
|   | 0.05 | 100 |
| 12 | 5 | 100 |
|   | 0.05 | 100 |
| 13 | 5 | 100 |
|   | 0.05 | 100 |
| 14 | 5 | 100 |
|   | 0.05 | 100 |

TABLE 3-continued

| Compound No. | Concentration (ppm) | Inhibitory rate (%) |
|---|---|---|
| 15 | 5 | 100 |
|    | 5 | 100 |
| 16 | 0.5 | 100 |
| A | 5 | 0 |

Test Example 4

Reproduction inhibitory activity against cotton aphids:

An emulsifiable concentrate prepared according to Formulation Example 1 was diluted with water to make a predetermined concentration. The dilution was sprayed onto potted cotton plants (in a stage of 8–9 days after sowing) infested with 1st instar nymphs of cotton aphids (*Aphis gossypii*) at a rate of 30 ml/2 pots on a turning table. Before spraying and one week after spraying, the number of nymphs and adults was counted, and a reproduction inhibitory index was expressed by the following equation:

$$\text{Reproduction inhibitory index} = \frac{\text{Number of individuals one week after spraying per 2 pots}}{\text{Number of individuals before spraying per 2 pots}}$$

wherein the judgement of activity is based on the following standard:

A: less than 1 (excellent effect)
B: from 1 to 3 (slight effect)
C: more than 3 (little effect)
D: same as in the untreated pots (no effect)

As a result, Compound No. 1 showed A as the reproduction inhibitory index at a concentration of 10 ppm.

What is claimed is:

1. A method for controlling insect pests belonging to Hemiptera which comprises applying to the insect pests or the locus where the insect pests propagate an effective amount of an amide derivative of the formula:

$$\underset{(R^2)_n}{\underset{\underset{5\phantom{x}6}{\underset{|}{\bigcirc}}}{R^1\underset{4\phantom{xx}1}{\overset{3\phantom{xx}2}{\phantom{\bigcirc}}}}}\text{—W—CH}_2\text{—CH}_2\text{—NH—}\overset{X}{\underset{\|}{C}}\text{—}\triangleleft$$

wherein $R^1$ is a group of the formula: $-Y-C_6H_{(5-m)}(R^4)_m$ or a group of the formula: $-Z-R^5$; $R^2$ is a hydrogen atom; $R^3$ is a chlorine atom; $R^4$ is, the same or different, a hydrogen atom, a fluorine atom, a chlorine atom or a methyl group; $R^5$ is a $C_3-C_6$ alkyl group or an alkoxyalkyl group having 3 to 6 carbon atoms; W is an oxygen atom; X is an oxygen atom or a sulfur atom; Y is an oxygen atom or a methylene group Z is an oxygen atom or a single bond when $R^5$ is a $C_3-C_6$ alkyl group, or a single bond when $R^5$ is an alkoxyalkyl group having 3 to 6 carbon atoms; n is a integer of 1; m is an integer 1 or 2.

2. A method for controlling insect pests belonging to planthoppers and leaf hoppers in a field of rice plants or aphids which comprises applying to the insect pests or the locus where the insect pests propagate an effective amount of an amide derivative of the formula:

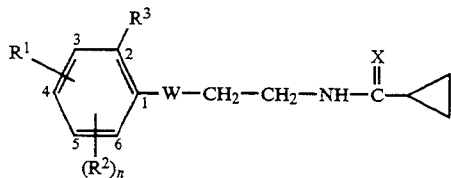

wherein $R^1$ is a group of the formula: $-Y-C_6H_{(5-m)}(R^4)_m$ or a group of the formula: $-Z-R^5$; $R^2$ is a hydrogen atom; $R^3$ is a chlorine atom; $R^4$ is, the same or different, a hydrogen atom, a fluorine atom, a chlorine atom or a methyl group; $R^5$ is a $C_3$-$C_6$ alkyl group or an alkoxyalkyl group having 3 to 6 carbon atoms; W is an oxygen atom; X is an oxygen atom or a sulfur atom; Y is an oxygen atom or a methylene group; Z is an oxygen atom or a single bond when $R^5$ is a $C_3$-$C_6$ alkyl group, or a single bond when $R^5$ is an alkoxyalkyl group having 3 to 6 carbon atoms; n is an integer of 1; m is an integer 1 or 2.

3. A method for controlling insect pests belonging to brown rice planthopper (*Nilaparvata lugens*) which comprises applying to the insect pests of the locus where the insect pests propagate an effective amount of an effective amount of an amide derivative of the formula:

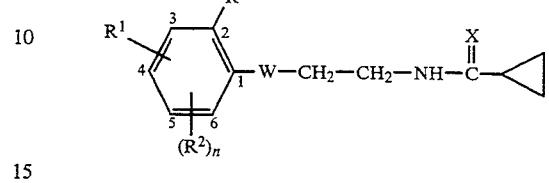

wherein $R^1$ is a group of the formula: $-Y-C_6H_{(5-m)}(R^4)_m$ or a group of the formula: $-Z-R^5$; $R^2$ is a hydrogen atom; $R^3$ is a chlorine atom; $R^4$ is, the same or different, a hydrogen atom, a fluorine atom, a chlorine atom or a methyl group; $R^5$ is a $C_3$-$C_6$ alkyl group or an alkoxyalkyl group having 3 to 6 carbon atoms; W is an oxygen atom; X is an oxygen atom or a sulfur atom; Y is an oxygen atom or a methylene group; Z is an oxygen atom or a single bond when $R^5$ is a $C_3$-$C_6$ alkyl group, or a single bond when $R^5$ is an alkoxyalkyl group having 3 to 6 carbon atoms; n is an integer of 1; m is an integer 1 or 2.

* * * * *

UNITED STATES PATENT AND TRADEMARK OFFICE
CERTIFICATE OF CORRECTION

PATENT NO. : 5,356,930
DATED : October 18, 1994
INVENTOR(S) : Hirosi KISIDA, Akira SHUTO, Noriyasu SAKAMOTO, Noritada MATSUO, Hiroaki FUJIMOTO and Kimitoshi UMEDA It is certified that error appears in the above-indentified patent and that said Letters Patent is hereby corrected as shown below:

On the title page,
Correcting the information in the section "[75] Inventors" such that the given name of the first-named inventor is changed from the incorrect spelling of "Hiroshi" to the correct spelling of --Hirosi--.

Signed and Sealed this

Seventh Day of February, 1995

Attest:

BRUCE LEHMAN

Attesting Officer *Commissioner of Patents and Trademarks*